United States Patent
Lidgard et al.

(10) Patent No.: US 10,702,250 B2
(45) Date of Patent: *Jul. 7, 2020

(54) SAMPLE COLLECTION DEVICE

(71) Applicant: Exact Sciences Corporation, Madison, WI (US)

(72) Inventors: Graham P. Lidgard, Madison, WI (US); Michael J. Domanico, Middleton, WI (US); Keith Fourrier, Madison, WI (US); James P. Light, II, Middleton, WI (US); Scott Castanon, Carlsbad, CA (US); Keith Kopitzke, Fallbrook, CA (US)

(73) Assignee: EXACT SCIENCES CORPORATION, Madison, WI (US)

( * ) Notice: Subject to any disclaimer, the term of this patent is extended or adjusted under 35 U.S.C. 154(b) by 438 days.

This patent is subject to a terminal disclaimer.

(21) Appl. No.: 15/671,379

(22) Filed: Aug. 8, 2017

(65) Prior Publication Data

US 2017/0333008 A1 Nov. 23, 2017

Related U.S. Application Data

(63) Continuation of application No. 14/939,671, filed on Nov. 12, 2015, now Pat. No. 9,750,482, which is a continuation of application No. 13/587,552, filed on Aug. 16, 2012, now Pat. No. 9,211,112.

(60) Provisional application No. 61/524,208, filed on Aug. 16, 2011.

(51) Int. Cl.
*A61B 10/00* (2006.01)
*G01N 1/38* (2006.01)
*B01L 3/00* (2006.01)

(52) U.S. Cl.
CPC ............ *A61B 10/0038* (2013.01); *G01N 1/38* (2013.01); *B01L 3/50825* (2013.01)

(58) Field of Classification Search
CPC .... A61B 10/0038; G01N 1/38; B01L 3/50825
USPC .......................................... 600/562, 570–572
See application file for complete search history.

(56) References Cited

U.S. PATENT DOCUMENTS

| 3,308,825 A | 3/1967 | Cruse |
| 4,027,658 A | 6/1977 | Marshall |
| 4,849,173 A | 7/1989 | Chang |
| 4,884,572 A | 12/1989 | Bays et al. |
| 4,981,143 A | 1/1991 | Sakita et al. |

(Continued)

FOREIGN PATENT DOCUMENTS

| EP | 0643131 | 3/1995 |
| EP | 0520443 | 1/1997 |

(Continued)

OTHER PUBLICATIONS

International Search Report and Written Opinion, dated Jan. 2, 2013, for International Patent Application PCT/US2012/051159 (10 pages).

(Continued)

*Primary Examiner* — Devin B Henson
*Assistant Examiner* — H. Q. Nguyen
(74) *Attorney, Agent, or Firm* — Casimir Jones, S.C.; Mary Ann D. Brow

(57) ABSTRACT

Provided herein is technology relating to collecting and preparing samples. For example, the technology relates particularly, but not exclusively, to devices, systems, and kits that allow a subject to collect and prepare a sample for analysis.

18 Claims, 11 Drawing Sheets

(56) References Cited

U.S. PATENT DOCUMENTS

| | | |
|---|---|---|
| 5,152,417 A | 10/1992 | Gallagher |
| 5,246,434 A | 9/1993 | Ebara |
| 5,316,732 A | 5/1994 | Golukhov et al. |
| 5,338,435 A | 8/1994 | Betts et al. |
| 5,440,942 A | 8/1995 | Hubbard et al. |
| 5,514,341 A | 5/1996 | Takeyoshi et al. |
| 5,543,115 A | 8/1996 | Karakawa et al. |
| 6,248,294 B1 | 6/2001 | Mason |
| 6,299,842 B1 | 10/2001 | Kozak et al. |
| 6,652,532 B2 | 11/2003 | Bonutti |
| 6,780,160 B2 | 8/2004 | Zhou et al. |
| 6,921,370 B2 | 7/2005 | Zhou et al. |
| 7,048,693 B2 | 5/2006 | Zhou et al. |
| 7,163,514 B2 | 1/2007 | Zhou et al. |
| 7,232,681 B2 | 6/2007 | O'Connell |
| 7,780,915 B2 | 8/2010 | Gao |
| 7,871,568 B2 | 1/2011 | Liang et al. |
| 7,908,935 B2 | 3/2011 | Hasegawa et al. |
| 8,241,227 B2 | 8/2012 | Ohnishi et al. |
| 8,252,229 B2 | 8/2012 | Thomas et al. |
| 8,562,919 B2 | 10/2013 | Shimada |
| 9,211,112 B2 | 12/2015 | Lidgard et al. |
| 9,750,482 B2 | 9/2017 | Lidgard et al. |
| 2005/0011821 A1 | 1/2005 | Held et al. |
| 2005/0036910 A1 | 2/2005 | Zhou et al. |
| 2005/0155440 A1 | 7/2005 | Kanjilal et al. |
| 2007/0208274 A1 | 9/2007 | Ostrowski et al. |
| 2008/0034899 A1 | 2/2008 | Kikuiri |
| 2008/0081341 A1 | 4/2008 | Maher et al. |
| 2009/0004058 A1 | 1/2009 | Liang et al. |
| 2009/0259142 A1 | 10/2009 | Lastella |
| 2010/0160830 A1 | 6/2010 | Schmiedl |
| 2010/0323343 A1 | 12/2010 | Egan et al. |
| 2011/0130681 A1 | 6/2011 | Okumura et al. |
| 2011/0244461 A1 | 10/2011 | Tanigami et al. |
| 2012/0083028 A1 | 4/2012 | Wu |

FOREIGN PATENT DOCUMENTS

| | | |
|---|---|---|
| EP | 1495811 | 1/2005 |
| EP | 1908522 | 12/2010 |
| EP | 2325619 | 5/2011 |
| JP | H07-140139 | 6/1995 |
| WO | 2010067534 | 6/2010 |

OTHER PUBLICATIONS

Extended European Search Report for EP12823519.9, dated Mar. 23, 2015, 7 pages.

FIG. 4
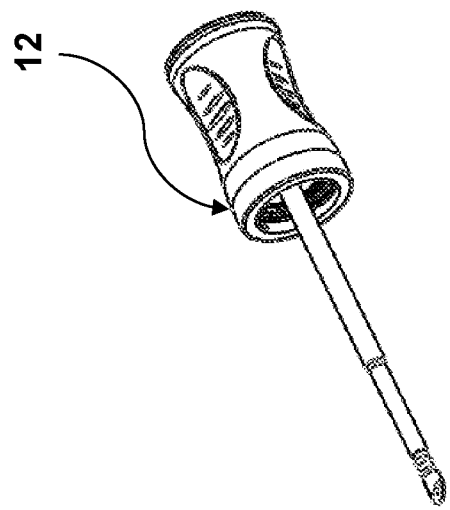
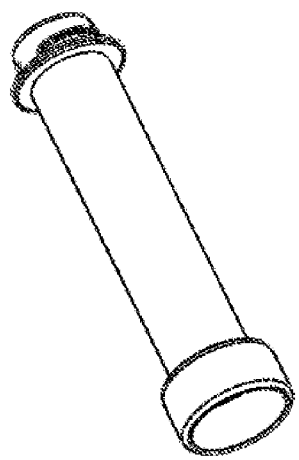
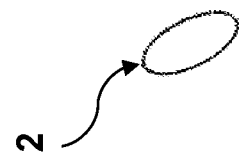

SAMPLE COLLECTION DEVICE

The present application is a continuation of U.S. patent application Ser. No. 14/939,671, filed Nov. 12, 2015, now allowed, which is a continuation of U.S. patent application Ser. No. 13/587,552, filed Aug. 16, 2012, now U.S. Pat. No. 9,211,112, which claims priority to U.S. Provisional Application Ser. No. 61/524,208, filed Aug. 16, 2011, each which is incorporated herein by reference.

FIELD OF INVENTION

Provided herein is technology relating to collecting and preparing samples. For example, the technology relates particularly, but not exclusively, to devices, systems, and kits that allow for the collection and preparation of a fecal sample for analysis.

BACKGROUND

Over 100,000 persons per year in the United States are afflicted with a cancer of the colon and rectum. When the number of colon and rectal cancers occurring each year is combined with the number of cancers occurring in other digestive organs, including the esophagus and stomach, cancers of the digestive system account for more occurrences of cancer than any other single form of the disease. Contrary to many other forms of cancer, early diagnosis and treatment of digestive tract cancer results in a cure rate of 80% to 90%. If, however, the disease is not detected until its later stages, the cure rate drops significantly. Thus, early detection of the disease is important for the successful treatment of digestive tract cancer.

Most cancers of the digestive tract bleed to a certain extent. This blood is deposited on and in fecal matter excreted from the digestive system. The presence of blood in fecal matter is not normally detected, however, until gross bleeding occurs—that is, until the blood is visible to the naked eye. Gross bleeding, however, is symptomatic of advanced cancers.

Early-stage digestive tract cancers, including pre-cancerous polyps, also tend to bleed, which produces occult (hidden) blood in the fecal matter. Other pathological conditions, such as Crohn's disease and diverticulitis, also produce occult blood in the fecal matter. Accordingly, test equipment and test procedures have been developed for use by physicians in testing for the presence of occult blood in fecal matter as an aid for diagnosing these and other medical conditions.

For example, a commonly used test for screening for colorectal cancer is a fecal occult blood test, which tests for the presence of hemoglobin in feces. The presence of hemoglobin in feces is an indicator of intestinal bleeding, which is frequently associated with colorectal cancer. When such fecal blood is detected, a patient can be referred for further medical testing.

Fecal immunochemical testing (FIT) is one type of assay used to detect hemoglobin indicative of fecal occult blood. FIT uses an antibody specific to the human globin protein of hemoglobin to measure the amount of blood in feces. To perform FIT on feces one first obtains a defined quantity of feces and suspend the sampled feces in a suitable liquid to prepare a feces suspension appropriate for testing. There is a need for a device that provides for an easy acquisition of a defined quantity of feces by a user and for the preparation and testing of a portion of the sample by a human or automated tester.

SUMMARY OF THE INVENTION

Accordingly, provided herein is a device for obtaining a fecal sample and preparing a suspension of the feces suitable for analysis, e.g., FIT. For example, in some embodiments, the technology comprises a device for collecting a sample, the device comprising a sample collection chamber bounded on a distal end by a penetrable seal and bounded on a proximal end by a septum, the septum comprising an aperture; a sampling rod adapted to fit through and seal the aperture, the sampling rod comprising a proximal portion having a proximal end, a distal portion having a distal end, an angled tip at the distal end, and at least one metering ridge near the distal end; and a solution comprising approximately 20 mM Tris (pH 7.4), 10% bovine serum albumen, 0.10% Tween-20, 0.095% sodium azide, 140 mM sodium chloride, 10 mM EDTA, and 15 µg/ml gentamicin. The metering ridge is designed for two primary purposes: first, the metering ridge provides a surface that facilitates the efficient acquisition of a fecal sample from a stool; second, the geometry of the metering ridge provides for the acquisition of a defined quantity (e.g., a volume or mass) of feces for the analysis. Embodiments of the metering ridges have particular designs and geometries that are advantageous for use of the sampling rod. For example, in some embodiments the metering ridge comprises a frustum of a cone, e.g., a right circular cone. Some embodiments provide that an axis of the frustum is coaxial with a longitudinal axis of the sampling rod and a base of the frustum faces the proximal end of the sampling rod. Moreover, in some embodiments the radius of the base of the frustum is approximately the same as the radius of the proximal end of the sampling rod. Some embodiments provide a series of metering ridges arranged in a "sawtooth" or "fish scale" pattern, e.g., in some embodiments the device comprises a plurality of stacked coaxial frusta to form a plurality of metering ridges.

During the development of particular embodiments of the technology, it was discovered that particular characteristics of the sampling rod are advantageous for use of the sampling rod. For example, in some embodiments the sampling rod is flexible, e.g., to allow it to bend. In some embodiments a cap is attached to the proximal end of the sampling rod, e.g., to seal the device, and in some embodiments a distal portion of the sampling rod has a radius approximately the same as the radius of the aperture and a proximal portion of the sampling rod has a radius larger than the radius of the aperture, e.g., to seal the aperture. That is, in some embodiments a junction of the distal portion with the proximal portion forms a stopper that seals the aperture when the distal portion is fully inserted through the aperture.

In some embodiments the device is designed to provide a metered sample for analysis. Specifically, after capturing a sample on the metering ridge, inserting the sampling rod through the aperture removes excess sample from the sampling rod and leaves a metered sample within the depressions of the metering ridge. The device is designed to provide access to the suspension of feces so that a portion is taken for testing by a human or an automated tester. Accordingly, in some embodiments the penetrable seal is penetrable by a pipette tip or needle. During the design of some embodiments of the device, it was discovered that an inserted pipette tip or needle sometimes collided with the sampling rod in the sample collection chamber. Such collisions may occur when a human is using a pipette or needle to obtain a portion of the suspension or when withdrawing the sample is automated, for example, by using robotics, and can result in errors in sampling or damage to sampling devices. As such, in some embodiments, the angled tip of the sampling rod deflects a pipette tip or needle that penetrates the penetrable seal. In some embodiments, the sampling rod is flexible and thus is able to move, e.g., to flex or bend in response to force, when a pipette tip or syringe needle collides with it.

The device is not limited in the types of samples that are obtained and prepared. Thus, while in some embodiments the device is used to sample feces, the sample in some embodiments is, for example, environmental matter (e.g., mud), biological matter (e.g., food), and industrial matter (e.g., sludge). Such examples are meant to be merely illustrative and not limiting and many other materials are suitable for sampling with the device.

The geometrical design of the device may take many forms. For example, in some embodiments the body is tubular, though it may also be square, rectangular, triangular, elliptical, or any other shape suitable to provide the required functions, e.g., manipulation of the device by a user and acquisition of a sample. Furthermore, the sampling rod may assume many forms. For example, in some embodiments the sampling rod is cylindrical.

In one aspect the device is designed for a user to provide a sample in one end and for a human or machine (e.g., a robot) tester to acquire a portion of the fecal suspension at the other end. Thus, embodiments provide devices comprising a penetrable seal through which a portion of the suspension is obtained. Some embodiments provide that the seal is made from foil. However, other materials are appropriate for the device provided the material seals the sample collection chamber while also being penetrable (e.g., by a pipette tip or by a syringe needle) such that a human or machine obtains a portion of the contents sealed within the sample collection chamber (e.g., a suspension of fecal matter in a solution). Some non-limiting examples of materials provided in various embodiments include paper, rubber, wax, and plastic.

Embodiments of the device have various physical characteristics with respect to materials and/or design. For example, embodiments of the device are made from, for example, polypropylene, polyethylene, polystyrene, and polytetrafluoroethylene. Moreover, in some embodiments the sample collection chamber has a volume of approximately 1-2 milliliters, in some embodiments the metering ridge provides a fecal sample of approximately 20 milligrams.

The devices provided herein find use in systems and kits for providing a fecal sample for testing. For example, some embodiments of the technology provided herein are systems for collecting a sample. These systems comprise a chamber functionality for holding a sample re-suspension solution, a penetrable seal functionality for sealing the chamber on one end and allowing access to the chamber by penetrating the seal functionality, a sampling functionality for contacting the sample and acquiring a portion of the sample, and a metering functionality for providing into the chamber functionality a defined volume of the acquired portion of the sample. Furthermore, the technology provides kits, embodiments of which comprise embodiments of the devices provided herein and an instruction for use. Moreover, in some embodiments the kits comprise a package in which to mail the collected sample.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 4 is an exploded view of an embodiment of the device provided herein.

DETAILED DESCRIPTION

Figure 1:
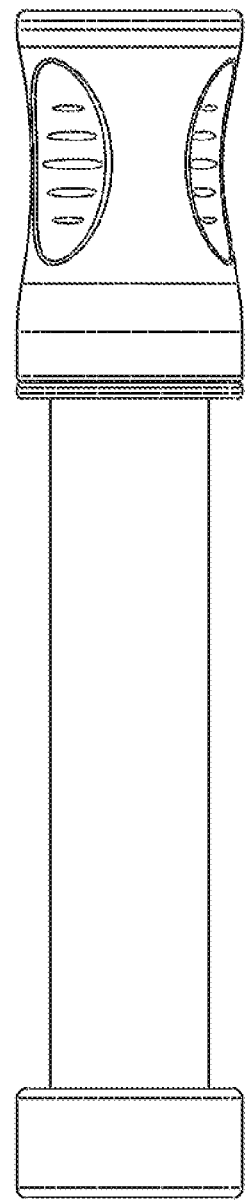
FIG. 1 is a side view of an embodiment of the device provided herein.

Provided herein is technology for acquiring a sample (e.g., a fecal sample) and preparing a suspension of the sample for analysis (e.g., a fecal immunochemical test). The device comprises two ends—one (proximal) end that is accessed by the user who acquires the sample and introduces it into the device for preservation and storage and the other (distal) end that is accessed by a human or automated tester for removing a portion of the resuspended sample for analysis. The features and components described herein combine to provide such functionality in a simple device that produces preserved and stable metered fecal samples for analysis (e.g., by FIT).

Definitions

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, a "penetrable seal" hermetically closes an opening of a chamber or enclosed space while the component is intact and is capable of being pierced or breached (e.g., by a needle or a pipette tip) to allow access to the contents sealed inside.

As used herein, the term "metered" means having a reasonably reproducible measured quantity.

Embodiments of the Technology

Although the disclosure herein refers to certain illustrated embodiments, it is to be understood that these embodiments are presented by way of example and not by way of limitation.

As shown by FIGS. 1-11, the device comprises as principal components a sampling rod, a body comprising a septum and a penetrable seal, and a solution. Embodiments of the device, particularly in reference to the interactions of these and other components, are described below.

1 Sampling Rod

The device comprises as a first component a sampling rod (5). As illustrated, e.g., in FIG. 2, the sampling rod (5) comprises a distal portion (7) and a proximal portion (6). In some embodiments the sampling rod is approximately 2.5 inches long. In certain preferred embodiments, the sampling rod is substantially circular in cross section for most of its length.

The proximal portion (6) of the sampling rod (5) is adapted for manipulation by a user and the distal portion (7) is adapted to acquire a metered sample. In some embodiments, a cap (12) is attached to the proximal end. In preferred embodiments, the cap (12) is adapted to mate with and close the proximal end of the body (1) (see below), for example, by mated threads on the cap (12) and body (1), by a snap closure, by a friction seal, or by other closures by which a cap securely closes a vessel to seal contents inside the vessel. In some embodiments, mated threads on the cap (12) and body (1) provide for securing the sampling rod (5) with a half-turn screw fit to the body (1). In some embodiments, the cap (12) comprises textured features that facilitate gripping and manipulating the sampling rod (5) by the user.

One or more metering ridges (9) is/are located near the tip (distal end) of the distal portion (7) of the sampling rod (5) (see FIGS. 2, 4, 5, and 8). In certain embodiments, each metering ridge is shaped like the frustum of a cone (e.g., a right circular cone, truncated by a plane parallel to the base). In preferred embodiments, the frustum has its base facing toward the proximal end of the sampling rod (5), and has its axis aligned with the longitudinal axis of the sampling rod. As is seen in the embodiments shown in the figures (e.g., FIG. 8), in some embodiments a series of axially aligned frusta are joined in some embodiments to make notched depressions in the distal end of the sampling rod (e.g., to form a serrated, saw tooth, or fish scale structure). In preferred configurations, the bases of the frusta have radii approximately the same as the radius of the distal portion of the sampling rod; thus, the radii of the tops of the frusta are smaller than the radius of the sampling rod.

The notched depressions of the metering ridges provide a structure within which to acquire a metered sample (e.g., a sample of approximately 20 milligrams). In use, rubbing and/or scraping the area comprising the metering ridges (9) on the stool to be sampled captures a mass of stool that covers the metering ridges (9) on the distal portion of the sampling rod. Furthermore, the metering ridges provide an effective way to collect a reasonably reproducible and defined volume and/or mass (e.g., approximately 20 milligrams) of feces for the sample. In particular, feces captured in the notched depressions remain associated with the sampling rod when the sampling rod is passed through a hole or aperture that is approximately the same radial size as the radius of the distal portion (7) of the sampling rod (5) (e.g., the aperture of the body septum as described below). The metering ridges comprise notched depressions having a defined volume for collecting a sample of a defined mass. Thus, when excess feces that is not present in the space defined by the notched depressions is scraped or rubbed from the sampling rod, e.g., by passage through an aperture, the feces remaining in the notched depressions has a volume defined by the size and shape of the notched depressions.

The sampling rod (5) is adapted to be inserted into the body (1), and, in particular, the sampling rod (5) is designed to fit through the body septum aperture, (a feature described in more detail below). Moreover, when inserted into the body (1), the sampling rod (5) is designed to seal the aperture (4) at the end of travel and thus seal the body sample collection chamber (10) (see below). In some embodiments, the device is designed to provide a seal at the aperture (4) that holds a minimum of 30 psi when internally pressurized with air. In particular, the sampling rod (5) comprises a proximal portion (6) and a distal portion (7). In certain preferred embodiments, the distal portion (7) has a radius that is smaller than the radius of the proximal portion (6) (see, e.g., the embodiment shown in FIGS. 2 and 8). Furthermore, in relation to the aperture (4) in the body septum (3), the radius of the distal portion (7) of the sampling rod (5) is smaller than the radius of the aperture (4) (e.g., very slightly smaller, such that excess feces is removed from the sampling rod (5) when the distal portion (7) passes through the aperture (4)), and the radius of the proximal portion (6) is larger than the radius of the aperture (4). Consequently, the junction of the proximal and distal portions of the sampling rod (5) forms a plug or stopper that seals the aperture (4) (and thus the sample collection chamber (10)) when the sampling rod (5) is substantially fully inserted into the body at the end of travel. In some embodiments, tightening the cap (12) onto the body (1) (e.g., by screwing) further secures the seal.

Figure 2:
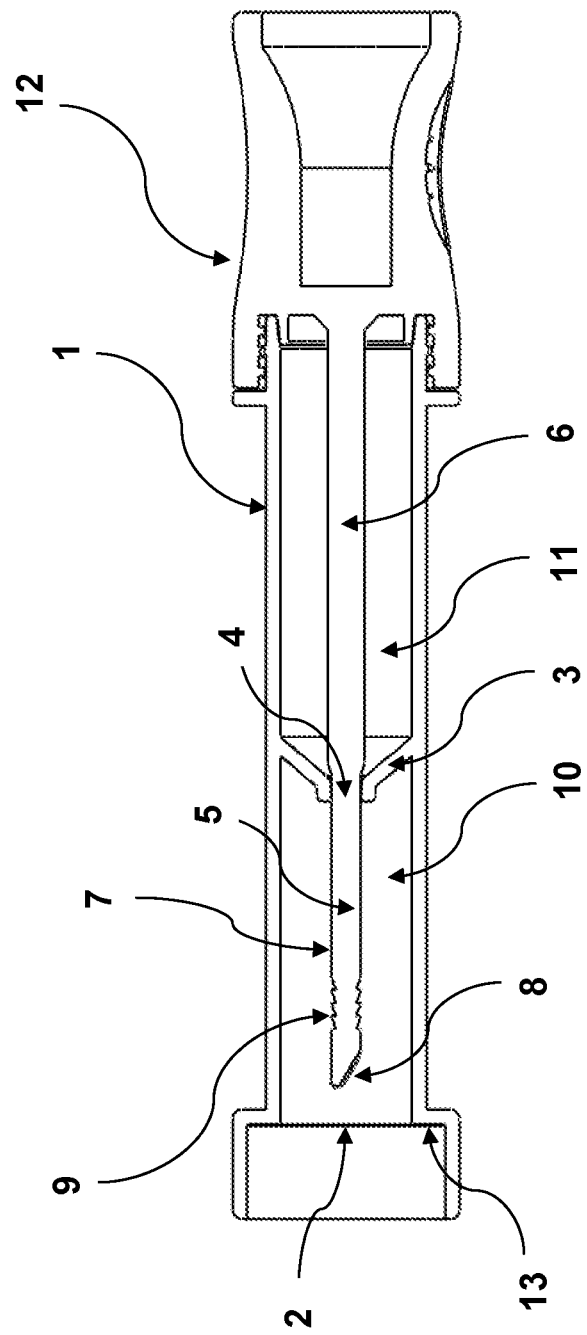
FIG. 2 is a side section view of an embodiment of the device provided herein, comprising a body (1) and a cap (12), the body (1) comprising proximal chamber (11) and a distal sample collection chamber (10). The distal sample collection chamber (10) is bounded on a distal end by a penetrable seal (2) on a sealing surface (13) on the body (1), and is bounded on a proximal end by a septum (3), the septum comprising an aperture (4). The cap (12) is affixed to the proximal end of a sampling rod (5) adapted to fit through and seal the aperture (4). The sampling rod (5) comprises a proximal portion (6), and a distal portion (7) having an angled tip (8) at the distal end and at least one metering ridge (9) near the distal end.
Figure 8:
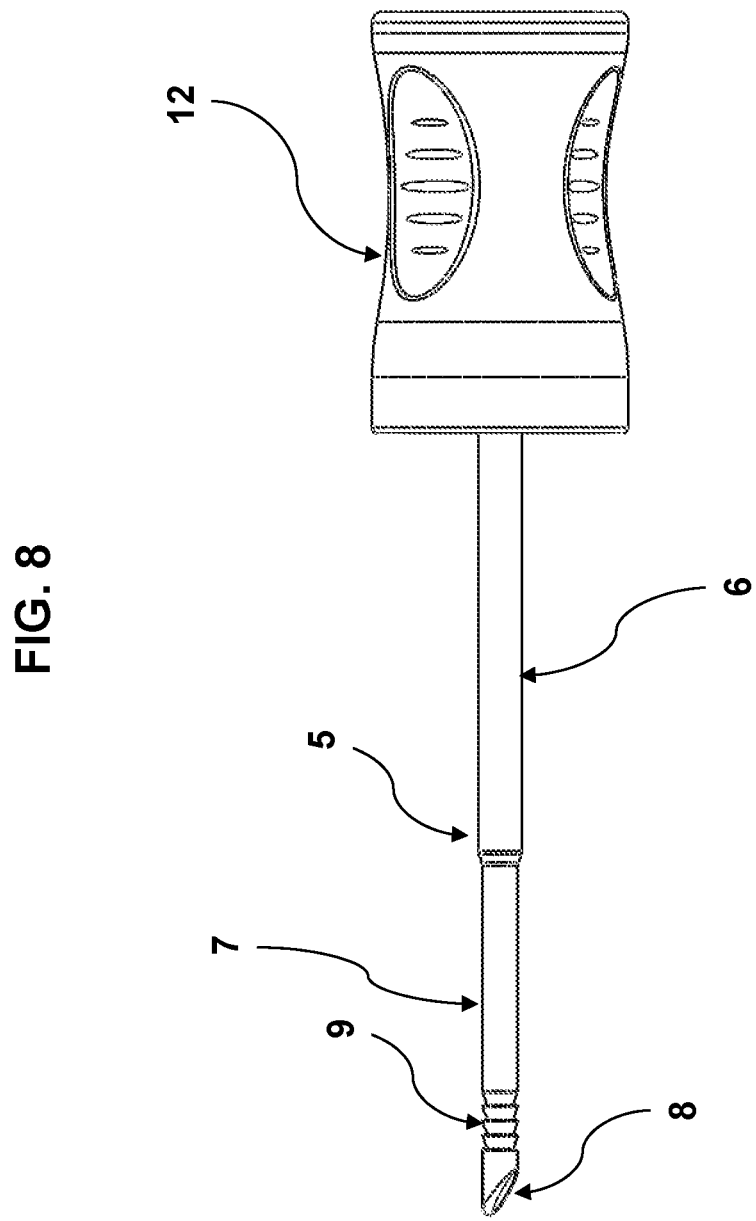
FIG. 8 is a side view of an embodiment of the sampling rod component.
Figure 9:
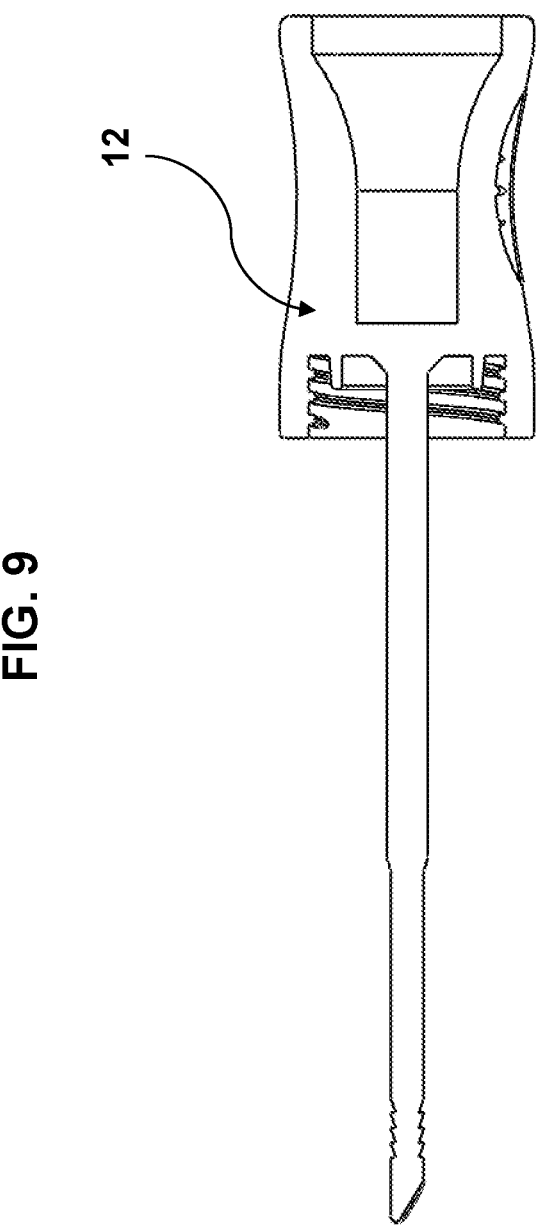
FIG. 9 is a side section view of an embodiment of the sampling rod component.
Figure 10:
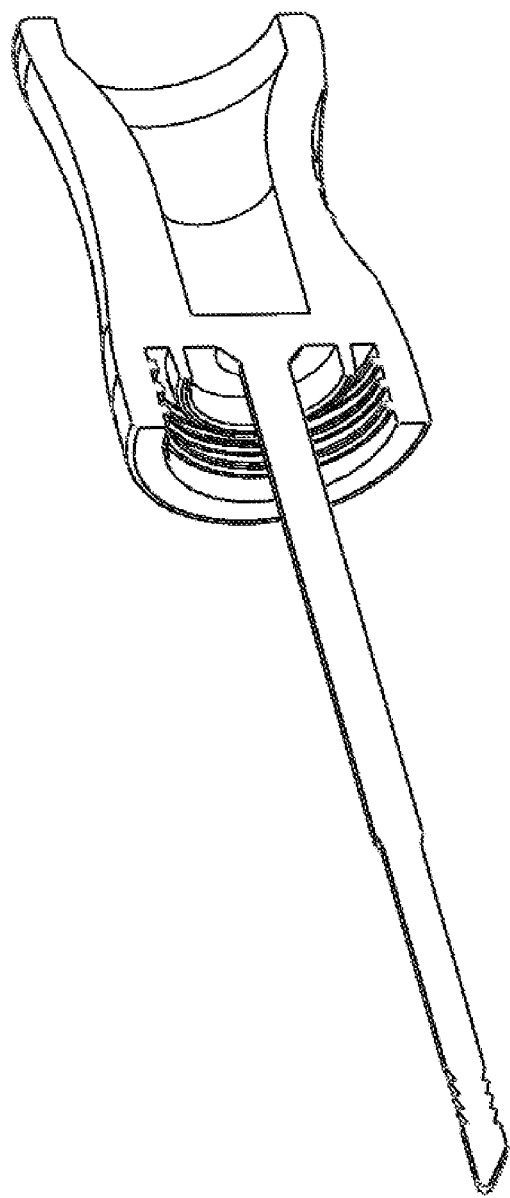
FIG. 10 is an isometric section view of an embodiment of the sampling rod component.
Figure 11:
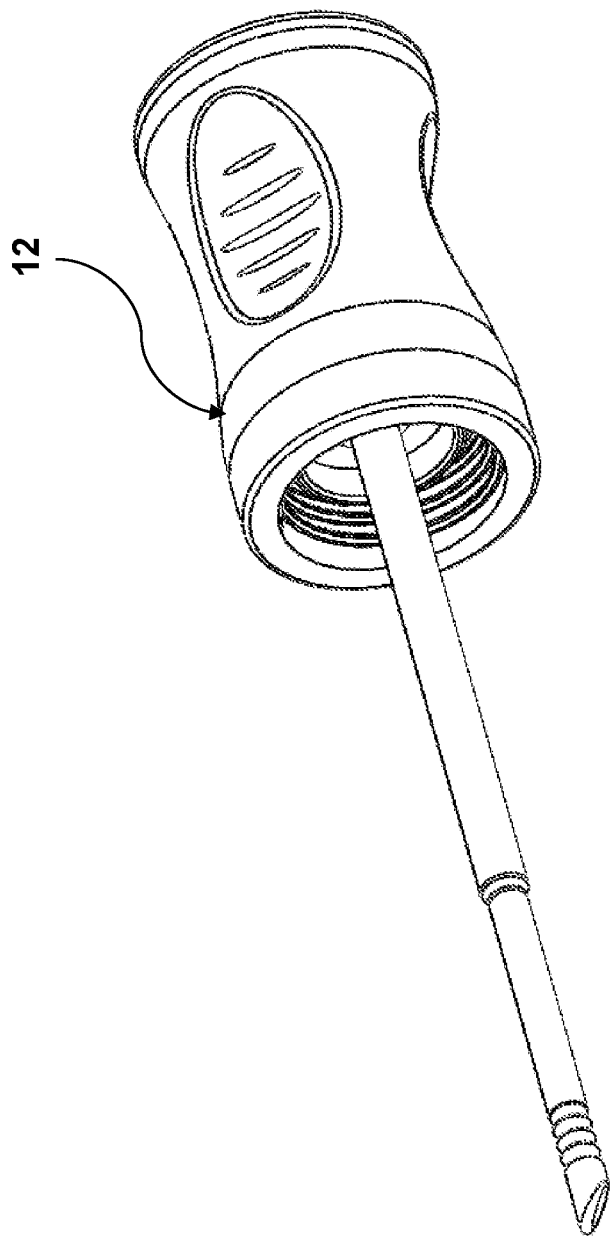
FIG. 11 is an isometric view of an embodiment of the sampling rod component.

In some embodiments, the distal tip (8) of the sampling rod is angled or beveled (see, e.g., (8) in the embodiments shown in FIGS. 2 and 8). When inserting a pipette tip or syringe needle into the distal end of the body (1) to withdraw an aliquot of the feces suspension (as described below), the tip or needle may sometimes collide with the sampling rod and consequently interrupt or otherwise compromise the withdrawal of the proper amount and/or damage the apparatus or machine used to withdraw the sample. While this is problematic for a human operator, a trained human can realize what has occurred and makes another attempt at withdrawing the proper volume as an aliquot for assay. However, in an automated setting wherein an autonomous robot or semi-autonomous system retrieves the aliquot, collision with the sampling rod may damage the machine and/or cause improper sampling. Consequently, an improper volume will be tested and produce an inaccurate and potentially misleading result (e.g., a false negative or false positive result). To minimize or eliminate such episodes, embodiments of the technology provide a sampling rod (5) with an angled tip (8) that, when inserted into the body (1) after acquiring a fecal sample, deflects collisions with an inserted pipette tip, syringe needle, or other implement inserted through the penetrable seal (2) e.g., to withdraw an aliquot of the fecal suspension. Moreover, in some embodiments, the sampling rod is made from a material that is flexible, so that it flexes or bends out of the way when a collision occurs. Deflection and/or flexing minimizes or eliminates the mechanical stress and trauma to the sampler and/or improper sampling that is associated with collisions and thus aids in maximizing the reproducibility of sampling and testing.

2 Body

The device comprises as another component a body (1). The body comprises a proximal chamber (11) and a distal sample collection chamber (10) (see, e.g., FIG. 2). The two chambers are separated by a septum (3), and the septum comprises an aperture (e.g., a hole, (4)) near its center that is just slightly large enough to allow passage of the distal portion (7) of the sampling rod (5) through it (see FIGS. 2 and 3). The long axis of the body has a length appropriate to contain the entirety of the sampling rod when the sampling rod is fully inserted into the body. In some embodiments, the outer diameter of the body is approximately 14 millimeters. When the sampling rod (5) is substantially fully inserted into the body (1) (e.g., at its end of travel into the body), the metering ridge (9) (and substantially all the acquired sample present within the notched depressions of the metering ridge) is located completely within the sample collection chamber (10) and thus is exposed there to any solution contained therein (see below). In preferred embodiments, the device is designed such that the sample contained within the metering ridge (9) contacts the solution in the sample collection compartment regardless of the orientation of the device.

The sample collection chamber (10) is bounded laterally by the body wall and on the proximal and distal ends by the septum (3) and by a penetrable seal (2) (see below, and FIG. 2, e.g.), respectively. In some embodiments, the proximal end of the body (1) is adapted to mate with a cap (12) attached to the proximal end of the sampling rod (5), for example, by means of mated threads on the cap and body (e.g., for securing the cap and sampling rod to the body with a half-turn screw), a snap closure, a friction seal, or other features by which a cap securely closes a vessel. See, e.g., body (1) and cap (12) in FIG. 2.

The body (1) is open on the distal end, e.g., the body comprises a hole on the distal end. The body (1) comprises a sealing surface (13) that is adapted to accept a penetrable seal on the distal end to cover the hole. See, e.g., sealing surface (13) in FIGS. 2, 3, and 6. In some embodiments the penetrable seal (2) is recessed. In certain preferred embodiments, the penetrable seal (2) is recessed approximately 0.125 inches with respect to the distal end of the body. In some embodiments the distal end of the body is adapted to accept a removable cover or cap, e.g., a pop-off cap, to protect the penetrable seal. In preferred embodiments, the diameter of the hole in the distal end of the body (1) is smaller than the width of the distal end of the body so that a ring of material is present on the distal end surrounding the hole, providing a surface on which to apply a penetrable seal (2). See, e.g., the sealing surface (13) in FIGS. 2 and 7. By affixing the penetrable seal (2) to the distal end of the body over the hole, the penetrable seal (2) hermetically closes the distal end of the body.

Figure 3:
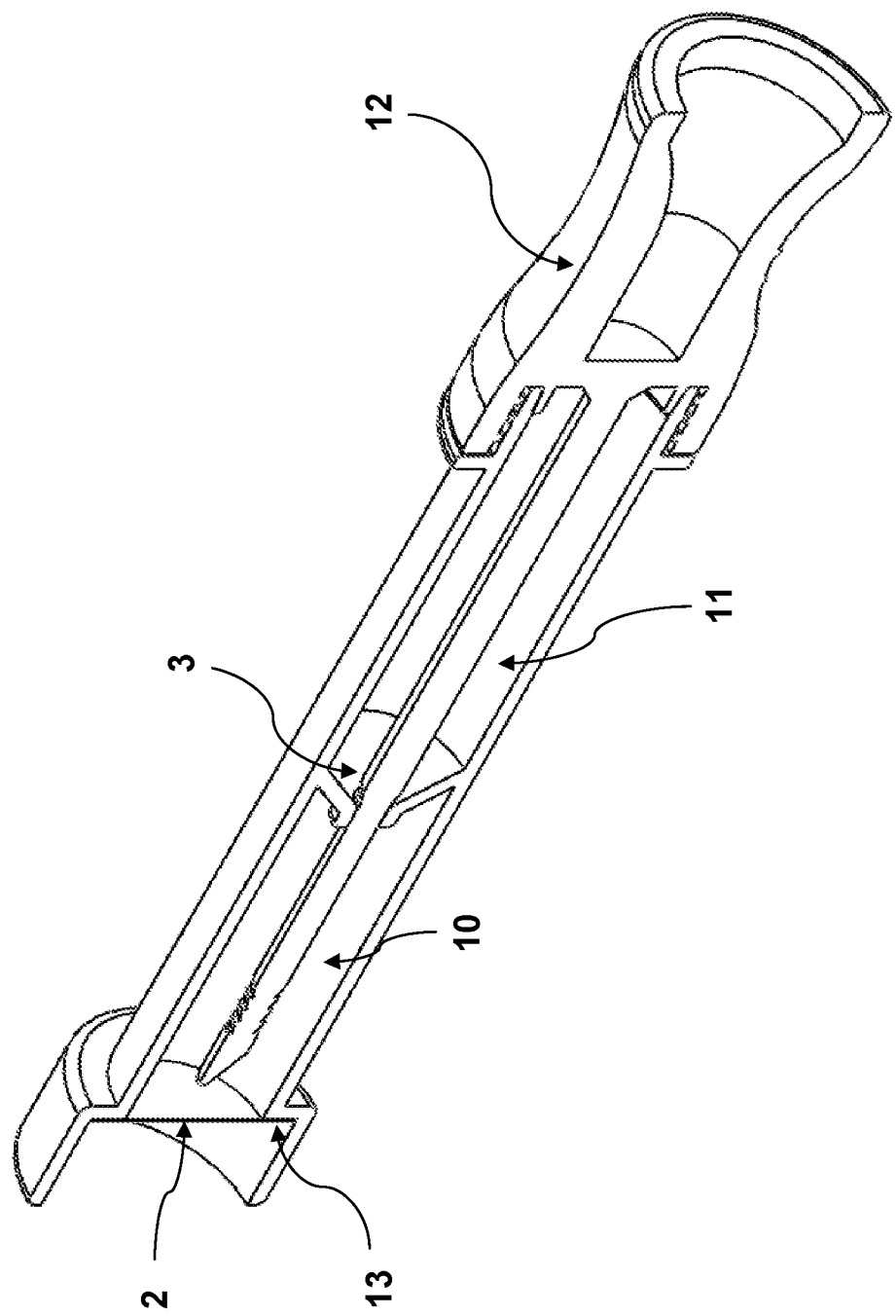
FIG. 3 is an isometric section view of an embodiment of the device provided herein.
Figure 5:
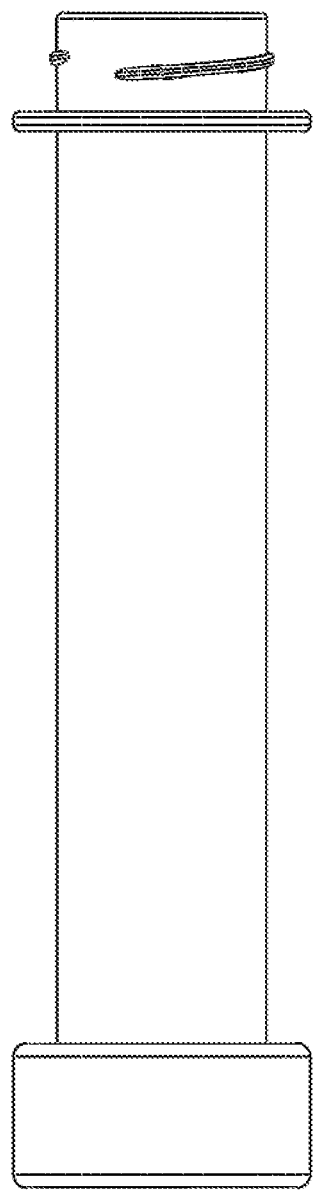
FIG. 5 is in a side view of an embodiment of the body component.
Figure 6:
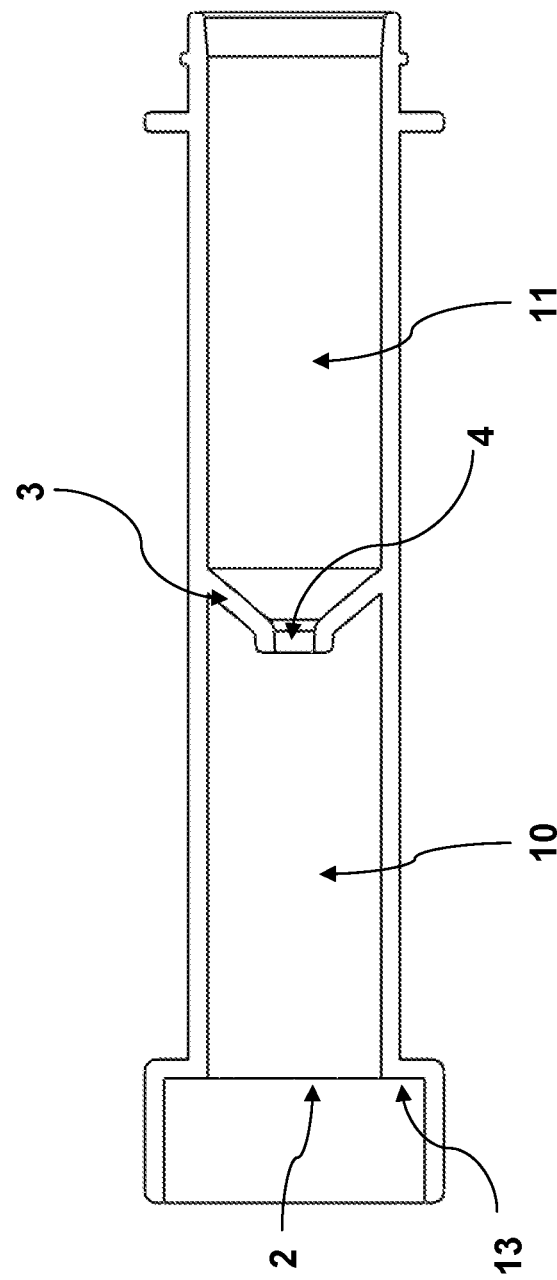
FIG. 6 is a side section view of an embodiment of the body component.
Figure 7:
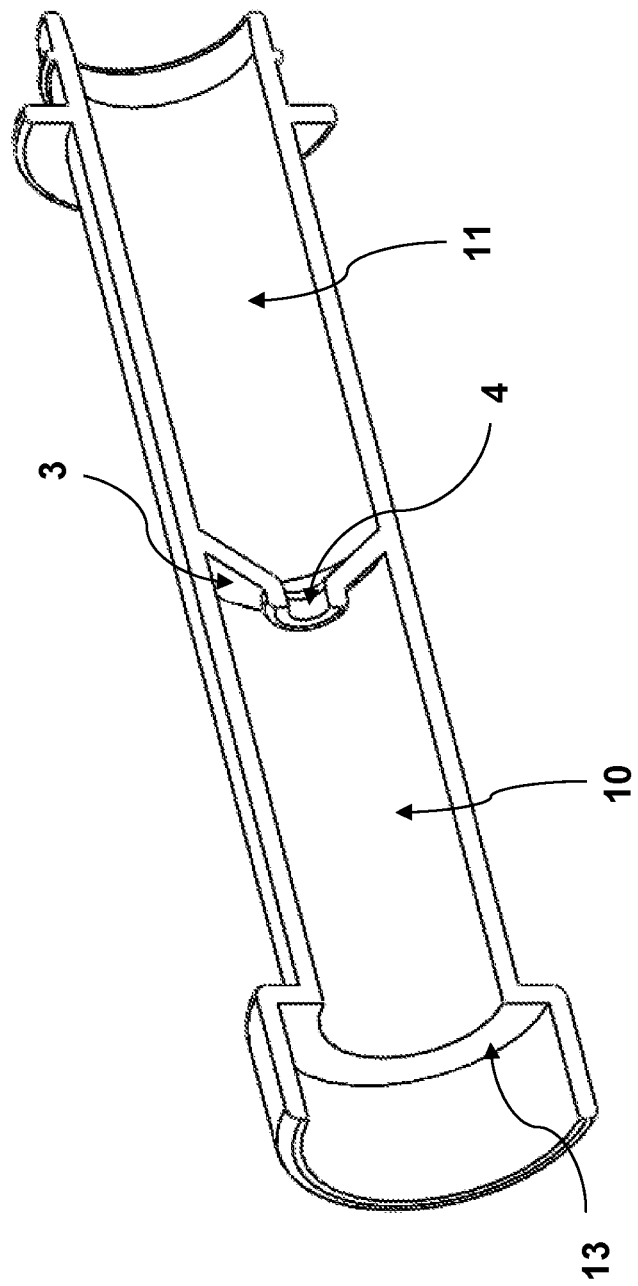
FIG. 7 is an isometric section view of an embodiment of the body component.

The sample collection chamber (e.g., sample collection chamber (10) in FIGS. 2 and 3) is adapted to hold a solution (e.g., the solution described below). In some embodiments, the sample collection chamber is adapted to hold a solution having a volume of approximately 2 milliliters. In some embodiments, when the sample collection chamber contains a solution, sample introduced into the chamber on the sampling rod is covered with the solution regardless of the orientation of the device. Furthermore, in certain preferred embodiments, when the sample collection chamber contains a solution, the sample collection chamber also holds a volume of air that allows for mixing of the sample with the solution. When the penetrable seal is secured to the distal end and the sampling rod is substantially fully inserted into the body to seal the aperture (e.g., at the end of travel for the sampling rod into the body), the solution is contained within the sample collection chamber such that it will not leak from the sample collection chamber. In some embodiments, the seal formed at the aperture holds a minimum of 30 psi when the device is internally pressurized with air. In some embodiments of the technology provided herein (e.g., embodiments of kits), the device is supplied to the end user in this type of a configuration (e.g., preloaded with solution and sealed by the sampling rod and penetrable seal).

3 Penetrable Seal

A third feature of the device is a penetrable seal. In preferred embodiments, the penetrable seal (2) is affixed to the distal end of the body to cover the hole on that end, thus sealing the sample collection chamber (10) on that end (and thus preventing the escape of any solution and/or sample that is contained inside). See, e.g., penetrable seal (2) in FIGS. 2, 3, and 4. The penetrable seal (2) is affixed to the body by any suitable means that adequately seals the distal end of the body, e.g., by an adhesive, crimping, friction, physical incorporation into the body when the body is molded, etc. For example, in some embodiments the penetrable seal is affixed to the body such that it provides a seal of the distal end that holds a minimum of 30 psi when the device is internally pressurized with air.

Furthermore, the penetrable seal is made from a material that can be penetrated, e.g., by a syringe needle or a pipette tip, to allow access to the sample collection chamber by a human user or an automated or semi-automated robot or other machine. Materials that are appropriate for the penetrable seal include, but are not limited to, foil, paper, rubber, plastic, and wax. The penetrable seal is made from a material that is chemically and biochemically compatible with the solution and samples that contact the device. The penetrable seal is strong enough to contain a solution securely (e.g., without leaking (e.g., the seal holds a pressure of 30 psi when internally pressurized with air)) within the sample collection space, while also being penetrable upon application of a low to moderate amount of force by a needle or pipette tip (e.g., a 1-milliliter pipette tip) pressed against the penetrable seal by a user, machine, or robot. For example, in some embodiments the penetrable seal comprises a laminated foil comprising a foil layer of approximately 0.001 inches and a polyester layer of approximately 0.005 inches. Such a foil product is available from commercial vendors (e.g., Hi-Tech Products). In some embodiments, other products are used that are suitable to meet the shelf life and sealing requirements.

4 Solution

The device comprises a solution in the sample collection chamber. In certain embodiments, the solution comprises Tris buffer, bovine serum albumin, Tween-20, sodium azide, sodium chloride, EDTA, and gentamicin. In preferred embodiments, the solution comprises the following components approximately in the indicated amounts and/or concentrations:

20 mil/Tris buffer (pH 7.4)
10% bovine serum albumen
0.10% Tween-20
0.095% sodium azide
140 mM sodium chloride
10 mil/EDTA
15 µg/ml gentamicin The solution comprises components to break up, solubilize, and/or suspend the sample such that withdrawal of a portion provides an aliquot suitable for analysis. In addition, the solution comprises components to stabilize, preserve, and/or protect the resulting suspension so that the analytes to be tested (e.g., globin) do not degrade or become damaged between the time the sample is acquired and the time the sample is tested. The solution thus helps to ensure that the analysis of the sample (e.g., a FIT) accurately reflects the analytes (e.g., globin) present in the sample when the sample was acquired.

5 Materials

The body (1), sampling rod (5), and cap (12) are made from a material that provides structural soundness to the device and that is chemically and biochemically compatible with the solution and samples that contact the device. Embodiments of the device are made from plastics such as, e.g., polypropylene, polyethylene, polystyrene, and polytetrafluoroethylene. The sampling rod (5) is made from a material that provides sufficient strength to the rod for collecting from relatively rigid samples. For example, in some embodiments the sampling rod is made from an opaque polypropylene and in some embodiments the sampling rod is made from a filled polypropylene. In some embodiments, the sampling rod is flexible and is thus made from a material that provides the appropriate flexibility, e.g., a flexible polypropylene. In some embodiments, the cap (12) and the body (5) are made of the same material. Moreover, in some embodiments the body is made from a transparent polypropylene. Different materials may be suitable for different applications and sample types, and, in some embodiments, the body and sampling rod are made from the same material and in some embodiments the body and sampling rod are made from different materials. In some embodiments, the materials and composition of the solution are chosen to provide a shelf-life for the device of approximately 2 years.

6 Use of the Device

The device is designed to provide an easy way to collect and produce fecal samples for analysis such as FIT. Accordingly, it is designed for use by both the sample taker and the sample tester. The sample taker may be, in some uses of the device, a person who does not have medical or clinical training, and thus the device is easy to use for such lay users in acquiring the sample. Thus, in some embodiments the body is composed of opaque material, or is covered, e.g., with a label, such that the interior components (e.g., the proximal and distal chambers, the septum, and the inserted sampling rod) are substantially blocked from view of a user, e.g., to avoid confusion regarding the proper use of the device.

At the same time, the device is designed within the appropriate tolerances and with a design that allows for precise and accurate analysis of the sample by a human or machine tester. Generally, the device will be provided to the sample provider in an assembled form—e.g., the sample collection chamber is filled with a volume of solution, the distal end of the body is sealed with the penetrable seal, and the sampling rod is fully inserted into the body such that the aperture is sealed.

Upon producing a stool, the sample provider removes the sampling rod (5) from the body (1) and scrapes or spears the stool with the sampling rod (5) to cover with stool the distal portion (7) of the sampling rod (5) comprising the metering ridge (9). The sampling rod (5) is then placed back into the body (1) by inserting the sampling rod (5) through the aperture (4) and securing the cap (12) to the body (1) (e.g., by screwing it onto the body by means of mated threads). When the sampling rod (5) is inserted through the aperture (4) in the body (1), stool not present in the notched depressions of the metering ridge (9) (e.g., excess stool) is rubbed and/or scraped from the sampling rod such that it remains in the proximal chamber (11) and outside the sample collection chamber (10). Consequently, only the feces associated with the metering ridge (9) is introduced into the sample collection chamber (10) and the solution present therein. The solution then acts to break up, solubilize, and/or suspend the sample. In addition, the solution comprises components to stabilize, preserve, and/or protect the suspension. The user then returns the device to a laboratory, clinic, or other location for analysis. In some embodiments, the device is designed to be appropriate for return by mail.

Next, the testing facility retrieves a portion of the feces suspension for analysis (e.g., by FIT). A user or machine penetrates the penetrable seal (2) (e.g., by a syringe needle or a pipette tip) to withdraw an aliquot of the suspension. The device is designed for manipulation by a human tester, an autonomous machine or robot, and/or a semi-autonomous machine, as appropriate for the analysis. After the required aliquot of the suspension is withdrawn, the device and remaining fecal sample suspension may then by discarded as appropriate.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A device for collecting a sample, the device comprising:
   a) a body comprising a sample collection chamber bounded on a distal end by a penetrable seal and bounded on a proximal end by a septum comprising an aperture, said penetrable seal being penetrable by a pipette tip or needle;
   b) a flexible sampling rod comprising a proximal portion and a distal portion, said sampling rod adapted to fit through and seal said aperture when said distal portion is in said sample collection chamber, wherein said distal portion comprises:
      i) an asymmetrical beveled tip at a distal end, said beveled tip having an apex at the circumference of the flexible sampling rod and configured to bend the flexible sampling rod away from collisions and/or to deflect collisions with an inserted pipette tip or needle; and
      ii) one or a plurality of metering ridges.

2. The device of claim 1 wherein at least one of said one or plurality of metering ridges comprises a frustum of a cone.

3. The device of claim 1 wherein a cap is attached to said proximal end of said sampling rod, wherein said cap is configured to engage a proximal end of said body.

4. The device of claim 3 wherein said cap and said proximal end of said body have mated threads for securing said cap to said body.

5. The device of claim 1 wherein said aperture has a radius, and wherein said distal portion of said sampling rod has a radius the same as said radius of said aperture and said proximal portion of said sampling rod has a radius larger than said radius of said aperture.

6. The device of claim 5 wherein a junction between said distal portion of said sampling rod and said proximal portion of said sampling rod forms a stopper that seals said aperture when said distal portion of said sampling rod is fully inserted through said aperture.

7. The device of claim 6 wherein said aperture when sealed is configured to hold 30 psi when the device is internally pressurized with air.

8. The device of claim 1 wherein the composition of said penetrable seal comprises one or more of:
   a) a foil;
   b) a foil layer and a polyester layer;
   c) a material selected from the group consisting of paper, rubber, wax, and plastic.

9. The device of claim 1 wherein said penetrable seal is configured to hold 30 psi when said device is internally pressurized with air.

10. The device of claim 1 wherein said body further comprises a sealing surface, wherein said penetrable seal is affixed to said sealing surface.

11. The device of claim 10 wherein said sealing surface is recessed.

12. The device of claim 1 further comprising a protective cap adapted to fit on a distal end of said body, wherein said cap covers said penetrable seal.

13. The device of claim 1, wherein said body is made from a material selected from the group consisting of polypropylene, polyethylene, polystyrene, and polytetrafluoroethylene.

14. The device of claim 1 wherein said sample collection chamber has a volume of 1-5 milliliters.

15. The device of claim 1, further comprising a solution in said sample collection chamber for preserving a suspended sample.

16. The device of claim 15, wherein said solution comprises Tris buffer, bovine serum albumen, polysorbate 20, sodium azide, sodium chloride, ethylenediaminetetraacetic acid, and gentamicin.

17. A kit for collecting a sample, the kit comprising:
   I) a device for collecting a sample, the device comprising:
      a) a body comprising a sample collection chamber bounded on a distal end by a penetrable seal and bounded on a proximal end by a septum comprising an aperture, said penetrable seal being penetrable by a pipette tip or needle;
      b) a flexible sampling rod comprising a proximal portion and a distal portion, said sampling rod adapted to fit through and seal said aperture when said distal portion is in said sample collection chamber, wherein said distal portion comprises:
         i) an asymmetrical beveled tip at a distal end, said beveled tip having an apex at the circumference of the flexible sampling rod and configured to bend the flexible sampling rod away from collisions and/or to deflect collisions with an inserted pipette tip or needle; and
         ii) one or a plurality of metering ridges; and
   II) an instruction for use.

18. The kit of claim 17, further comprising a package in which to mail said device containing a collected sample.

* * * * *